United States Patent [19]

Fedorov et al.

[11] Patent Number: 4,647,282

[45] Date of Patent: Mar. 3, 1987

[54] MATERIAL FOR OCULAR PROSTHETICS

[75] Inventors: Svyatoslav N. Fedorov; Eleonora V. Egorova; Sergei R. Nanushyan; Evgeny A. Chernyshev; Oleg P. Spiridonov; Igor L. Benenson; Alexandr N. Polivanov; Anatoly S. Shapatin; Alexandr A. Karavaev, all of Moscow, U.S.S.R.

[73] Assignee: Moskovsky Nauchno-Issledovatelsky Institut Mikrokhirurgii Glaza; Gosudarstvenny Nauchno-Issledovatelsky Institut Khimii I Tekhnologii Elementoorganicheskikh Soedineniy; Moskovsky Institut Elektronnogo Mashinostrogenia, all of Moscow, U.S.S.R.

[21] Appl. No.: 769,931

[22] Filed: Aug. 27, 1985

[51] Int. Cl.[4] .................. C08G 77/04; C08G 77/08; A61F 2/14

[52] U.S. Cl. .......................... 623/4; 623/5; 623/6; 623/66; 523/106; 523/107; 351/160 R; 526/279

[58] Field of Search ............... 623/4, 5, 6, 66; 523/106, 107; 351/160 R; 526/279

[56] References Cited

U.S. PATENT DOCUMENTS

| 4,139,513 | 2/1979 | Tanaka | 523/107 |
| 4,463,149 | 7/1984 | Ellis | 523/107 |
| 4,507,452 | 3/1985 | Foley | 523/107 |

Primary Examiner—Richard J. Apley
Assistant Examiner—Greg Beaucage
Attorney, Agent, or Firm—Fleit, Jacobson, Cohn & Price

[57] ABSTRACT

An optical prosthetic device made from a material based on silicone compounds is a cured composition resulting from vulcanization of a mixture of α,ω-bis-trivinylsiloxyoligodimethyl(methylphenyl)-siloxane and α,ω-bis-trimethyl(dimethylhydro)siloxyoligomethyl(phenyl)methylhydro-siloxane in the presence of a polyaddition reaction catalyst based on the compounds of metals of the platinum group, the ratio of the first mixture component to the second one ranging within 100:1 and 100:20 parts by mass.

1 Claim, No Drawings

MATERIAL FOR OCULAR PROSTHETICS

FIELD OF THE INVENTION

The present invention relates to ophthalmology and is particularly concerned with materials for ocular prosthetics. The invention can find widespread application in diverse sight correction techniques for making a variety of optical correcting elements, in particular, prosthetic crystalline lenses or lenticuli, and also for partial substitution of injured ocular structures.

BACKGROUND OF THE INVENTION

Materials for ocular prosthetics now in current use must satisfy a number of rather strict requirements, the principal ones being as follows: the materials in question should feature high mechanical properties, be optically transparent and biologically intert towards the ocular structures and the intraocular humor. It is quite expedient that the materials applied for ocular prosthetics have as low density as possible and be elastic.

Known in the art is use for ocular prosthetics of such materials as glass, polymers, in particular, polymethylmethacrylate, and liquid silicone.

However, properties of the materials used place not infrequently substantial limitation upon their application in the field of eye surgery. To take an example, liquid silicones are successfully applicable solely for partial substitution of the vitreous body in case of vitrectomy. Polymethylmethacrylate that has found extensive application as a material for making lenticuli is in fact too stiff of a material, which compels surgeons to considerably enlarge the operative wound. Glass has not so far found fairly broad application due to its high specific density.

SUMMARY OF THE INVENTION

It is an object of the present invention to provide a material for eye surgery, which would feature low density, good mechanical characteristics and high optical properties, elasticity and be biologically inert with respect to the ocular tissues and the intraoscular humor.

It is another object of the present invention to provide such a material that, apart from featuring all the aforestated properties, would possess good processability, i.e., would enable formation of, e.g., lenticuli in a single production process.

The aforesaid and other objects are accomplished due to the fact that the material for eye surgery, according to the invention, is a silicone-based compound made from a cured composition resulting from vulcanization of a mixture of $\alpha,\omega$-bis-trivinylsiloxyoligodimethyl (methylphenyl-siloxane and $\alpha,\omega$-bis-trimethyl(dimethylhydro)siloxyoligomethyl(phenyl)methylhydro-siloxane in the presence of a polyaddition reaction catalyst based on the compounds of metals of the platinum group, the ratio of the first mixture component to the second one rabging within 100:1 and 100:20 parts by mass.

It has been found that the ratio of the first component to the second one may not exceed 100:1 as otherwise the mechanical strength of, e.g. a lenticulus made from the material under consideration is so reduced that it cannot be implanted in the eye without its deformation, nor may said ratio be less than 100:20, since at lower ratios the number of postoperative complications increases due to too high stiffness acquired by the lenticulus and enhanced adhesive properties of the material at elevated temperatures.

DESCRIPTION OF THE PREFERRED EMBODIMENTS

In what follows the invention will be illustrated in a description of some specific but not limiting embodiments of producing the material according to the invention.

Example 1

There are intermixed for a few minutes manually or with the use of a mechanical stirrer, 15 g $\alpha,\omega$-bis-trivinylsiloxyoligodimethyl-siloxane (hereinafter referred to as Component I), and 0.15 g $\alpha,\omega$-bis-trimethyloxyoligodimethylmethylhydro-siloxane (Component II) until complete homogenization of the composition. Then added to the resultant mixture is 0.08 g one percent solution of, e.g., $H_2PtCl_6.6H_2O$ in insopropanol as a catalyst. The mixture is stirred, exposed to vacuum to eliminate the occluded air, and dispensed in the appropriate moulds made of fluorinated plastic or of a specially treated metal, to obtain a required item. Then thus-filled mould is placed in a temperature-controlled cabinet at 130° to 180° C. and allowed to stand there for 0.5 to 2 hours. Once the mould has been cooled, the finished product is extracted therefrom.

The material of the invention involving other ratios of the Components I and II is prepared in a similar way. Some other ratios of the components are tabulated in Table 1 below, wherein the physico-mecanical characteristics of the material are specified.

Example 2

Whenever necessity arises in use of a material featuring higher refractive index, a mixture of 15 g $\alpha,\omega$-bis-trivinylsiloxyoligodimethylmethylphenyl-siloxane, 0.45 g $\alpha,\omega$-bis-trimethylsiloxyoligodimethylmethylphenyl-methylhydro-siloxane, and 0.15 g one-percent solution of $H_2PtCl_6.6H_2O$ in tetrahydrofuran in a way similar to Example 1. Further treatment is conducted as described in Example 1. For the physico-mechanical characteristics of the product refer to Table a below.

Example 3

Whenever it becomes necessary to use a material having increased elasticity, a mixture of 15 g $\alpha,\omega$-bis-trivinylsiloxyoligodimethylmethylphenyl-siloxane, 1.5 g $\alpha,\omega$-bis-dimethylhydrosiloxyoligodimethylmethylphenylmethylhydro-siloxane, and 0.1 g of a catalyst, which is in fact a one-percent solution of a complex compound, resulting from interreaction of $H_2PtCl_6.6H_2O$ with 1,1,3,3-tetramethyl-1.3-divinyl-disiloxane, in isopropanol.

Principal mechanical and optical characteristics of the materials obtained according to the aforedescribed Examples are tabulated below.

TABLE 1

| Ratio of Components I and II | Density, g/cm³ | Refractive index | Light transmission factor, % | Ultimate tensile strength, MPa | Percentage elongation |
|---|---|---|---|---|---|
| Example 1 | | | | | |
| 100:1 | 0.99 | 1.410 | 98.5 | 4.0 | 120 |
| 100:10 | 0.97 | 1.408 | 99.0 | 3.5 | 100 |
| 100:20 | 0.95 | 1.405 | 99.0 | 3.0 | 100 |
| Example 2 | | | | | |

TABLE 1-continued

| Ratio of Components I and II | Density, g/cm³ | Refractive index | Light transmission factor, % | Ultimate tensile strength, MPa | Percentage elongation |
|---|---|---|---|---|---|
| 100:3 | 1.13 | 1.480 | 98.5 | 2.5 | 130 |
| Example 3 | | | | | |
| 100:10 | 1.05 | 1.430 | 98.0 | 3.0 | 200 |

The material according to the invention can also be made as a thin film or sheeting of any arbitrary thickness and is applied to good advantage, e.g., for substitution of an injured portion of the iris. Whenever it is desirable to attain a cosmetic effect, some organic dyes or inorganic pigments can be added to the material to give a required tint thereto.

When the material according to the invention is used for making lenticuli, the prepared liquid mixture is cast into a mould, whose geometric parameters, alongside with the refractive index of the material, defines the dioptry of the lenticulus being produced and the dimensions of its optical portion. The supporting portion of the lenticulus is shaped in this case as, e.g., a thin film.

Lenticuli made from the material according to the invention, exhibit twice as high optical resolution as compared with those made from polymethylmethacrylate and feature higher light transmission factor. Adequate elasticity of the material enables one to implant the lenticuli in the eye in a folded state, which makes it possible to considerably reduce (from 8 mm to 3 mm) the size of the operative wound. All this reduces much the number of the intra- and postoperative complications and cuts down radically the duration of the postoperative period.

Better processability of the material according to the invention resides in that preconditioning of the original stock, its polymerization and moulding, e.g., a lenticulus are as a whole an integral and continuous production process. The process incorporates also hot sterilization of the material, whereby the products from the material can be applied immediately after their production in the operating room. It is also worth noting that the hot sterilization of the material is in fact the simplest, safest and most reliable one.

Studies into toxicological properties of the material according to the invention in experiments on test animals have demonstrated that only the material in question is characterized by a nonreactive coursing of the postoperative period, which makes it possible to cut down the reahabilitation period of the prosthetophakial patients. Histological examinations show a minimized traumatic effect that might be inflicted upon the intraocular structures.

Clinical approvement of the lenticulus made from the material according to the invention has been carried out in more than 200 patients of the various age groups. The implanted lenticulus exhibits its indifference to the biological tissues from the first day after surgery. The postoperative inflammatory symptoms are much less pronounced compared with implantation of conventional polymethylmethacrylate lenticuli. The light-refracting ocular media restore their transparency three times as fast. Clinical reflecting microscopy of the corneal endothelium carried out before and within different follow-up periods, has demonstrated a lower traumatic effect of the material involved. Acuity of vision in all the patients operated upon is stable, being within 0.8 and 1.0 in a majority of the patients.

Implantation of a lenticulus made from the material of the invention is performed as follows. A 4 to 5 mm incision is carried out under local anethesia from 11 to 13 o'clock of the dial. The anterior capsule is slit open horizontally, or in the form of a triangale with its vertex facing 12 o'clock. The nucleus and the lenticular mass are removed typically of, e.g., extracapsular cataract extraction. Then the lenticulus held in a fenestrated forceps is inserted, under the control of a spatula, between the capsular leaflets in the lower segment. Next the forceps and spatula are removed, whereupon the upper pole of the lenticulus is fitted between the capsular leaflets in the upper segment, using a broad spatula and the iris tenaculum. Thereupon the anterior chamber is restored, hermetically sealing sutures are placed and a monocular patch is applied. As a result of surgery the lentoculus is fixed in the equatorial zone of the lens capsule, while its optical portion is fixed strictly with respect to the eye optical axis.

Given below are some clinical case histories as examples.

Female patient Ch., 44, was operated upon her left eye, i.e., extracapsular extraction of a complicated cataract followed by implantation of a $19.0^D$ lenticulus. Surgery uneventful. A nonreactive postoperative coursing was observed from the first day after surgery. The operated eye was quiet, the light-refracting media transparent. Acuity of vision before and after surgery, 0.16 and 1.0, respectively. Follow-up observations of the patient within one year demonstrated stability of the visual functions, normal hemo- and hydrodynamic ocular indices. Special examinations (endothelial microscopy and fluorescent iridoangiography) demonstrated normal conditions and good stable functions of the intraocular structures. The lenticulus was found to assume the correct and stable position with respect to the eye optical axis.

Female patient A., 34, was operated upon for phako-emulsification of a traumatic cataract, excision of the posterior capsule, and implantation of a $20.0^D$ lenticulus. Surgery uneventful. The postoperative period practically nonreactive. Visual acuity before surgery-motion of patient's hand before her face, after surgery, 1.0. Follow-up observations within a two-year period demonstrated complete stabilization of the visual functions and good conditions of the intraocular structures. The implanted lenticulus in a correct position, stably centred with respect to the eye optical axis.

What we claim is:

1. A lens or other optical prosthetic device comprising a cured composition resulting from vulcanization of a mixture of α,ω-bis-trivinylsiloxyoligodimethyl(methylphenyl)-siloxane and α-ω-bis-trimethyl(dimethylhydro)siloxyoligomethyl(phenyl)methylhydro-siloxane in the presence of a polyaddition reaction catalyst based on the compounds of metals of the platinum group, the ratio of the first mixture component to the second one ranging within 100:1 and 100:20 parts by mass.

* * * * *